United States Patent
Li et al.

(10) Patent No.: US 12,404,231 B2
(45) Date of Patent: Sep. 2, 2025

(54) METHOD FOR PREPARING TRIFLUOROMETHYL AROMATIC COMPOUND

(71) Applicant: JINGDEZHEN FUSHINE LIFE TECHNOLOGY CO., LTD., Jingdezhen (CN)

(72) Inventors: Huiyue Li, Jingdezhen (CN); Yinghui Chen, Jingdezhen (CN); Jinhua Yan, Jingdezhen (CN); Haihong Wen, Jingdezhen (CN); Jian Yao, Jingdezhen (CN); Weifeng Tao, Jingdezhen (CN)

(73) Assignee: Jingdezhen Fushine Life Technology Co., Ltd., Jingdezhen (CN)

( * ) Notice: Subject to any disclaimer, the term of this patent is extended or adjusted under 35 U.S.C. 154(b) by 0 days.

(21) Appl. No.: 18/857,747

(22) PCT Filed: Mar. 7, 2024

(86) PCT No.: PCT/CN2024/080491
§ 371 (c)(1),
(2) Date: Oct. 17, 2024

(87) PCT Pub. No.: WO2025/156371
PCT Pub. Date: Jul. 31, 2025

(65) Prior Publication Data
US 2025/0257028 A1 Aug. 14, 2025

(30) Foreign Application Priority Data
Jan. 24, 2024 (CN) .......................... 202410102233.6

(51) Int. Cl.
*C07C 209/84* (2006.01)
*C07C 209/74* (2006.01)
(52) U.S. Cl.
CPC .......... *C07C 209/84* (2013.01); *C07C 209/74* (2013.01)
(58) Field of Classification Search
None
See application file for complete search history.

(56) References Cited

U.S. PATENT DOCUMENTS 6,417,361 B1    7/2002    Hayashi et al.

FOREIGN PATENT DOCUMENTS

| CN | 1218447 A | 6/1999 |
|---|---|---|
| CN | 102701904 A | 10/2012 |
| CN | 103113345 A | 5/2013 |
| CN | 106866509 A | 6/2017 |
| CN | 114195635 A | 3/2022 |
| CN | 114874179 A | 8/2022 |
| CN | 117164549 A | 12/2023 |
| CN | 117362262 A | 1/2024 |
| GB | 2003474 A | 3/1979 |
| WO | WO 2006090210 | * 8/2006 |

OTHER PUBLICATIONS

First Office Action received in Chinese Application No. 202410102233. 6, The State Intellectual Property Office of People's Republic of China, mailed Aug. 2, 2024.
International Search Report received in Patent Cooperation Treaty Application No. PCT/CN2024/080419, ISA: CN, mailed Sep. 27, 2024.

* cited by examiner

*Primary Examiner* — Renee Claytor
*Assistant Examiner* — Jennifer C Sawyer
(74) *Attorney, Agent, or Firm* — CM Law PLLC; Robert C. Klinger

(57) ABSTRACT

Provided is a method for preparing a trifluoromethyl aromatic compound, including: mixing a trichloromethyl aromatic compound with an organic alkali hydrofluoride to obtain a mixture, and subjecting the mixture to fluorination to obtain a reaction solution; subjecting the reaction solution to solid-liquid separation to obtain an organic alkali hydrochloride wet product and a filtrate, drying the organic alkali hydrochloride wet product, and condensing and recycling a gas generated during the drying to obtain a condensed product; and purifying the filtrate and the condensed product by rectification to obtain the trifluoromethyl aromatic compound.

7 Claims, No Drawings

METHOD FOR PREPARING TRIFLUOROMETHYL AROMATIC COMPOUND

CROSS REFERENCE TO RELATED APPLICATION

The present application is a national stage application of International Patent Application PCT/CN2024/080491, filed on Mar. 7, 2024, which claims priority to the Chinese Patent Application No. CN202410102233.6, filed with the China National Intellectual Property Administration (CNIPA) on Jan. 24, 2024, and entitled "METHOD FOR PREPARING TRIFLUOROMETHYL AROMATIC COMPOUND". The disclosure of the two applications is incorporated herein by reference in its entirety.

TECHNICAL FIELD

The present disclosure relates to the technical field of trifluoromethyl compounds, and in particular to a method for preparing a trifluoromethyl aromatic compound.

BACKGROUND

Trifluoromethyl group has a strong electron attracting capacity and lipophilic property, and its C—F bond is extremely stable. Introducing the trifluoromethyl group into organic compounds can change the properties of the organic compounds, such as polarity and stability. Aromatic compounds containing the trifluoromethyl group are widely used in the fields such as medicine and pesticides.

Trifluoromethyl benzene compounds and trifluoromethyl pyridine compounds are two types of common trifluoromethyl aromatic compounds and are important intermediates for fluorine-containing pesticides, fluorine-containing dyes, and fluorine-containing pharmaceuticals. Furthermore, most of them are also used as excellent solvents in organic synthesis in the chemical industry and have extremely wide applications.

Currently, the preparation of the trifluoromethyl aromatic compounds generally uses a trichloromethyl aromatic compound as the starting raw material and hydrogen fluoride as the fluorinating agent for the synthesis. For example, Chinese patent application with a publication number CN106866509A provides a method for preparing 2-fluoro-5-trifluoromethylpyridine, in which 3-methylpyridine is used as a raw material and subjected to chlorination to obtain 2-chloro-5-trichloromethylpyridine, which is then subjected to fluorination using anhydrous hydrogen fluoride as a fluorinating agent to obtain 2-fluoro-5-trifluoromethylpyridine. Chinese patent application with a publication number CN114195635A discloses a method for synthesizing 2-(trifluoromethyl)benzoyl chloride, in which 1-(dichloromethyl)-2-(trichloromethyl)benzene is obtained by chlorination, which is prepared into 1-(dichloromethyl)-2-(trifluoromethyl)benzene by using hydrogen fluoride as a fluorinating agent, which is then subjected to hydrolysis and acylating chlorination to obtain a target product.

In summary, the current preparation of trifluoromethyl aromatic compounds mostly depends on hydrogen fluoride as a fluorination agent. Due to the use of hydrogen fluoride, most reactions need to be conducted under high pressures, which not only cause high safety risks, but also have difficult-to-control side reactions, resulting in an unstable product quality. Moreover, residual fluoride ions in the by-product hydrochloric acid are difficult to remove, thereby limiting applications of the by-product hydrochloric acid and then invisibly increasing an environmental protection cost.

SUMMARY

In view of this, the present disclosure provides a method for preparing a trifluoromethyl aromatic compound. In the present disclosure, an organic alkali hydrofluoride is used as a fluorinating reagent, the method does not require high-pressure conditions and exhibits desirable safety, and the product has stable quality. Moreover, the produced organic alkali hydrochloride can be sold as a by-product with significant economic benefits.

To achieve the above object, the present disclosure provides the following technical solutions:

A method for preparing a trifluoromethyl aromatic compound is provided, including:
  mixing a trichloromethyl aromatic compound with an organic alkali hydrofluoride to obtain a mixture, and subjecting the mixture to fluorination to obtain a reaction solution;
  subjecting the reaction solution to solid-liquid separation to obtain an organic alkali hydrochloride wet product and a filtrate, drying the organic alkali hydrochloride wet product, and condensing and recycling a gas generated during the drying to obtain a condensed product; and
  purifying the filtrate and the condensed product by rectification to obtain the trifluoromethyl aromatic compound.

In some embodiments, the trichloromethyl aromatic compound includes one selected from the group consisting of a trichloromethyl benzene compound and a trichloromethyl pyridine compound; the trichloromethyl benzene compound has a structure as shown in Formula I; and the trichloromethyl pyridine compound has a structure as shown in Formula II;

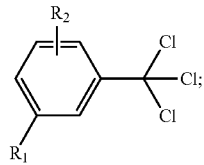

Formula I

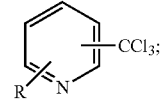

Formula II wherein
  in Formula I: $R_1$ is halogen and $R_2$ is —$NO_2$; and in Formula II: R is halogen.

In some embodiments, the organic alkali hydrofluoride includes an organic amine hydrofluoride.

In some embodiments, the organic amine hydrofluoride includes one or more selected from the group consisting of a pyridine hydrofluoride, a triethylamine hydrofluoride, a diethylamine hydrofluoride, a trimethylamine hydrofluoride, a dimethylamine hydrofluoride, and a monomethylamine hydrofluoride.

In some embodiments, a molar ratio of the trichloromethyl aromatic compound to the organic alkali hydrofluoride is in a range of 1: (1-3).

In some embodiments, the fluorination is conducted at a temperature of 80° C. to 140° C. for 5 h to 20 h.

In some embodiments, the drying is conducted by vacuum drying, and the drying is conducted at a temperature of 70° C. to 80° C. under a vacuum degree of −0.09 MPa to −0.095 MPa for 10 h to 16 h.

In some embodiments, an organic alkali hydrochloride is obtained by drying; and the method further includes: after the drying, neutralizing the organic alkali hydrochloride with a liquid alkali obtain a neutralized product, and subjecting the neutralized product to distillation and dehydration to obtain a free organic alkali.

In some embodiments, purifying the filtrate and the condensed product by rectification is conducted at a vacuum degree of 100 Pa to 200 Pa, and a top temperature of the rectification is at a temperature of 80° C. to 100° C. below a boiling point of the trifluoromethyl aromatic compound.

In some embodiments, under the condition that a pot residue obtained from the rectification comprises one or more selected from the group consisting of the trichloromethyl aromatic compound, a monofluoro substitute and a difluoro substitute thereof, the method further comprising: returning the pot residue obtained from the rectification to the fluorination for reuse.

The present disclosure provides a method for preparing a trifluoromethyl aromatic compound, including: mixing a trichloromethyl aromatic compound with an organic alkali hydrofluoride to obtain a mixture, and subjecting the mixture to fluorination to obtain a reaction solution; subjecting the reaction solution to solid-liquid separation to obtain an organic alkali hydrochloride wet product and a filtrate, drying the organic alkali hydrochloride wet product, and condensing and recycling a gas generated during the drying to obtain a condensed product; and purifying the filtrate and the condensed product by rectification to obtain the trifluoromethyl aromatic compound. In the present disclosure, the organic alkali hydrofluoride is used as a fluorinating reagent, the fluorination does not require high-pressure conditions and has mild reaction conditions and desirable safety, and the product has stable quality. Moreover, the organic alkali hydrofluoride is of low cost, which is beneficial for reducing production costs. Moreover, the produced organic alkali hydrochloride can be sold as a by-product with significant economic benefits.

In addition, in the present disclosure, taking advantage of the large difference between the boiling point of the trifluoromethyl aromatic compound and the boiling point of the organic alkali hydrochloride, during the drying of the organic alkali hydrochloride wet product, the trifluoromethyl aromatic compound produced during the drying is condensed and recycled, thereby further improving the yield of the trifluoromethyl aromatic compound. Meanwhile, residual fluoride ions in the by-product hydrochloride can be avoided, thereby improving the quality of the by-product hydrochloride.

Furthermore, in the present disclosure, the residual pot residue of the rectification is returned to the fluorination to continue participating in the fluorination. The main components of the residual pot residue of the rectification are the trichloromethyl aromatic compound and monofluoro substitute and difluoro substitute thereof, which are returned to the fluorination to further improve the utilization of raw materials and the yield of products.

In conclusion, the method for the trifluoromethyl aromatic compound provided by the present disclosure has an effective conversion rate of not less than 95% and a comprehensive molar yield of not less than 95%. The by-product hydrochloride is dissociated by the liquid alkali, and the dissociated by-product hydrochloride is distilled and dehydrated, and dried to obtain the by-product organic alkali which meets industry standards, and can be sold as an industrial by-product. Therefore, the method does not produce any hazardous waste except a small amount of wastewater. Therefore, the method provided by the present disclosure has high efficiency, economy, and environmental friendliness.

DETAILED DESCRIPTION OF THE EMBODIMENTS

The present disclosure provides a method for preparing a trifluoromethyl aromatic compound, including:
   mixing a trichloromethyl aromatic compound with an organic alkali hydrofluoride to obtain a mixture, and subjecting the mixture to fluorination to obtain a reaction solution;
   subjecting the reaction solution to solid-liquid separation to obtain an organic alkali hydrochloride wet product and a filtrate, drying the organic alkali hydrochloride wet product, and condensing and recycling a gas generated during the drying to obtain a condensed product; and
   purifying the filtrate and the condensed product by rectification to obtain the trifluoromethyl aromatic compound.

In the present disclosure, a trichloromethyl aromatic compound is mixed with an organic alkali hydrofluoride to obtain a mixture, and the mixture is subjected to fluorination to obtain a reaction solution. In some embodiments of the present disclosure, the trichloromethyl aromatic compound includes one selected from the group consisting of a trichloromethyl benzene compound and a trichloromethyl pyridine compound; the trichloromethyl benzene compound has a structure as shown in Formula I; and the trichloromethyl pyridine compound has a structure as shown in Formula II;

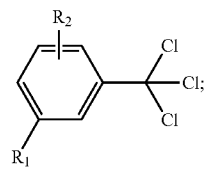

Formula I

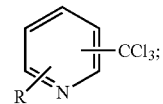

Formula II wherein
   in Formula I: $R_1$ is halogen and $R_2$ is —$NO_2$; and in Formula II: R is halogen.

In some embodiments of the present disclosure, $R_1$ in Formula I is a meta-substituent of a trichloromethyl group, preferably Cl or Br, and more preferably Cl; $R_2$ in Formula I is a nitro group, which is located at an ortho, meta, or para position of a trichloromethyl group, and preferably at the meta-position of the trichloromethyl group.

In some embodiments of the present disclosure, R in Formula II is Cl or Br, and preferably Cl; a trichloromethyl group in Formula II is in an ortho, meta, or para position of a N atom, and R is in an ortho, meta, or para position of a trichloromethyl group.

In some embodiments of the present disclosure, the trifluoromethyl aromatic compound is a trifluoromethyl benzene compound or a trifluoromethyl pyridine compound; the trifluoromethyl benzene compound has a structure as shown in Formula II; and the trifluoromethyl pyridine compound has a structure as shown in Formula IV;

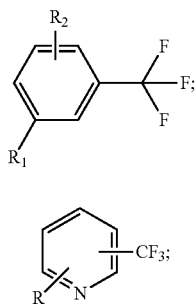

Formula III

Formula IV wherein in Formula III: $R_1$ is halogen and $R_2$ is —$NO_2$; and in Formula IV: R is halogen.

In the present disclosure, the types and positions of $R_1$ and $R_2$ in Formula III are the same as those in Formula I, and they will not be repeated here; the types and positions of R in Formula IV are the same as those in Formula II, and they will not be repeated here.

In some embodiments of the present disclosure, the trichloromethyl aromatic compound includes 2-trichloromethyl-4-nitrochlorobenzene or 3-trichloromethyl-6-chloropyridine; and the trifluoromethyl aromatic compound includes 2-trifluoromethyl-4-nitrochlorobenzene or 3-trifluoromethyl-6-chloropyridine.

In the present disclosure, under the condition that the trichloromethyl aromatic compound is the trichloromethyl benzene compound, a final product is the trifluoromethyl benzene compound, and a reaction formula is shown in Formula A:

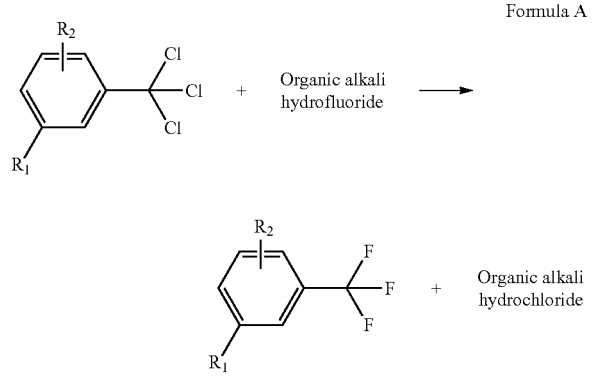

Formula A

In the present disclosure, under the condition that the trichloromethyl aromatic compound is the trichloromethyl pyridine compound, a final product is the trifluoromethyl pyridine compound, and a reaction formula is shown in Formula B:

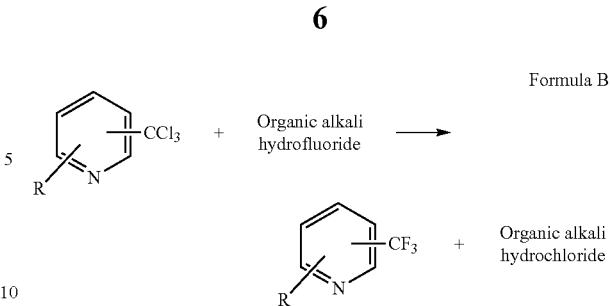

Formula B

In some embodiments of the present disclosure, the organic alkali hydrofluoride includes an organic amine hydrofluoride; the organic amine hydrofluoride includes one or more of a pyridine hydrofluoride, a triethylamine hydrofluoride, a diethylamine hydrofluoride, a trimethylamine hydrofluoride, a dimethylamine hydrofluoride, and a monomethylamine hydrofluoride; and a molar ratio of the trichloromethyl aromatic compound to the organic alkali hydrofluoride is in a range of 1: (1-3), preferably 1: (1-1.5).

In some embodiments of the present disclosure, the fluorination is conducted at a temperature of 80° C. to 140° C., and preferably 100° C. to 120° C.; and the fluorination is conducted for 5 h to 20 h, and preferably 10 h to 15 h. In some embodiments of the present disclosure, the fluorination is conducted at an atmospheric pressure without additional control of the reaction pressure; and the fluorination is conducted under stirring. In some embodiments of the present disclosure, the trichloromethyl aromatic compound and the organic alkali hydrofluoride are added into a reaction container, heated to a fluorination temperature under stirring, and subjected to reaction under a heat preservation condition; after the fluorination is completed, a resulting product is cooled to room temperature.

In the present disclosure, after obtaining the reaction solution, the reaction solution is subjected to solid-liquid separation to obtain an organic alkali hydrochloride wet product and a filtrate, the organic alkali hydrochloride wet product is dried, and a gas generated during the drying is condensed and recycled to obtain a condensed product. In some embodiments of the present disclosure, the solid-liquid separation is conducted by filtration or centrifugation; the drying is conducted by vacuum drying; the drying is conducted at a temperature of 70° C. to 80° C., and preferably 75° C. to 80° C.; the drying is conducted for 10 h to 16 h, and preferably 12 h to 14 h; and the drying is conducted under a vacuum degree of preferably −0.09 MPa to −0.095 MPa. During the drying, the trifluoromethyl aromatic compound forms a gaseous state, and is recycled by condensation to further improve the product yield, reduce the fluorine content in the organic alkali hydrochloride, and improve the quality of the by-product.

In some embodiments of the present disclosure, an organic alkali hydrochloride is obtained by drying; and the organic alkali hydrochloride is neutralized with a liquid alkali to obtain a neutralized product, and then the neutralized product is subjected to distillation and dehydration to obtain a free organic alkali.

In the present disclosure, after obtaining the filtrate and the condensed and recycled condensed product, the filtrate and the condensed product are purified by rectification to obtain the trifluoromethyl aromatic compound. In some embodiments of the present disclosure, the filtrate and the condensed product are combined and then purified; the purifying is conducted by rectification; a device for the rectification is a rectification column; the rectification is conducted at a vacuum degree of 100 Pa to 200 Pa; and a top temperature of the rectification is determined according to a boiling point of the target product, specifically 80° C. to 100° C. below the boiling point of the target product. The product is collected at a top of the rectification column. In some embodiments of the present disclosure, under the condition that a pot residue obtained from the rectification includes one or more selected from the group consisting of the trichloromethyl aromatic compound, and a monofluoro substitute and a difluoro substitute thereof, the pot residue is returned to the fluorination for reuse, which can improve the utilization rate of the raw materials and the product yield.

The technical solutions of the present disclosure will be clearly and completely described below with reference to the specific examples of the present disclosure. Obviously, the described examples are only a part of, not all of, the examples of the present disclosure. All other embodiments obtained by those skilled in the art based on the embodiments of the present disclosure without creative efforts shall fall within the scope of the present disclosure.

Example 1

275 g of 2-trichloromethyl-4-nitrochlorobenzene (MW=274.9, 1.0 mol) and 136 g of triethylamine hydrofluoride (MW=121.2, 1.1 mol) were successively added into a three-necked flask, stirred, and heated to a temperature of 100° C. to 110° C., and then reacted at the temperature for 15 h. A resulting reaction product was then cooled, and filtered to obtain a triethylamine hydrochloride wet product and a filtrate. The triethylamine hydrochloride wet product was vacuum dried at 80° C. for 14 h under a vacuum degree of −0.095 MPa to obtain 135 g of a by-product triethylamine hydrochloride, while an evaporated gas during the drying was condensed to obtain recycled 2-trifluoromethyl-4-nitrochlorobenzene. The filtrate and the recycled 2-trifluoromethyl-4-nitrochlorobenzene were combined, and rectified by a rectification column, controlling a pressure within 200 Pa and a top temperature of 65° C. to 75° C. A positive boiling product was collected to obtain 215 g of 2-trifluoromethyl-4-nitrochlorobenzene with a purity of 99.6%. 2-monofluoromethyl-4-nitrochlorobenzene, 2-difluoromethyl-4-nitrochlorobenzene, and 2-trifluoromethyl-4-nitrochlorobenzene in a residual pot residue obtained from the rectification each had a content of 33 wt %, 56 wt %, and 8.5 wt %. The pot residue was returned to the fluorination for reuse, and a product obtained from a pot residue after reusing had an average molar yield of 95%.

Example 2

231 g of 3-trichloromethyl-6-chloropyridine (MW=230.9, 1.0 mol) and 148.6 g of pyridine hydrofluoride (MW=99.1, 1.5 mol) were successively added into a three-necked flask, stirred, and heated to a temperature of 110° C. to 120° C., and then reacted at the temperature for 12 h. A resulting reaction product was then cooled, and filtered to obtain a pyridine hydrochloride wet product and a filtrate. The pyridine hydrochloride wet product was vacuum dried at 80° C. for 14 h under a vacuum degree of −0.095 MPa to obtain 110 g of a by-product pyridine hydrochloride, while an evaporated gas during the drying was condensed to obtain recycled 2-trifluoromethyl-6-chloropyridine. The filtrate and the recycled 2-trifluoromethyl-6-chloropyridine were combined, and rectified by a rectification column, controlling a pressure within 200 Pa and a top temperature of 80° C. to 90° C. A positive boiling product was collected to obtain 175 g of 3-trifluoromethyl-6-chloropyridine with a purity of 99.4%. 3-monofluoromethyl-6-chloropyridine, 3-difluoromethyl-6-chloropyridine, and 3-trifluoromethyl-6-chloropyridine in a residual pot residue obtained from the rectification each had a content of 29.8 wt %, 51 wt %, and 10.6 wt %. The pot residue was returned to the fluorination for reuse, and a product obtained from a pot residue after reusing had an average molar yield of 96.6%.

Example 3

275 g of 2-trichloromethyl-4-nitrochlorobenzene (MW=274.9, 1.0 mol) and 70 g of dimethylamine hydrofluoride were successively added into a three-necked flask, stirred, and heated to a temperature of 100° C. to 110° C., and then reacted at the temperature for 15 h. A resulting reaction product was then cooled, and filtered to obtain a dimethylamine hydrochloride wet product and a filtrate. The dimethylamine hydrochloride wet product was vacuum dried at 75° C. for 14 h under a vacuum degree of −0.095 MPa to obtain 79 g of a by-product dimethylamine hydrochloride, while an evaporated gas during the drying was condensed to obtain recycled 2-trifluoromethyl-4-nitrochlorobenzene. The filtrate and the recycled 2-trifluoromethyl-4-nitrochlorobenzene were combined, and rectified by a rectification column. controlling a pressure within 200 Pa and a top temperature of 65° C. to 75° C. A positive boiling product was collected to obtain 213 g of 2-trifluoromethyl-4-nitrochlorobenzene with a purity of 99.7%. 2-monofluoromethyl-4-nitrochlorobenzene, 2-difluoromethyl-4-nitrochlorobenzene, and 2-trifluoromethyl-4-nitrochlorobenzene in a residual pot residue obtained from the rectification each had a content of 32 wt %, 57 wt %, and 8.7 wt %. The pot residue was returned to the fluorination for reuse, and a product ontained from a pot residue after reusing had an average molar yield of 94.8%.

Example 4

275 g of 2-trichloromethyl-4-nitrochlorobenzene (MW=274.9, 1.0 mol) and 95 g of trimethylamine hydrofluoride (MW=79.1, 1.2 mol) were successively added into a three-necked flaske, stirred, and heated to a temperature of 100° C. to 110° C., and then reacted at the temperature for 15 h. A resulting reaction product was then cooled, and filtered to obtain a trimethylamine hydrochloride wet product and a filtrate. The trimethylamine hydrochloride wet product was vacuum dried at 75° C. for 14 h under a vacuum degree of −0.095 MPa to obtain 110 g of a by-product trimethylamine hydrochloride, while an evaporated gas during the drying was condensed to obtain recycled 2-trifluoromethyl-4-nitrochlorobenzene. The filtrate and the recycled 2-trifluoromethyl-4-nitrochlorobenzene were combined, and rectified by a rectification column, controlling a pressure within 200 Pa and a top temperature of 65° C. to 75° C. A positive boiling product was collected to obtain 210 g of 2-trifluoromethyl-4-nitrochlorobenzene with a purity of 99.5%. 2-monofluoromethyl-4-nitrochlorobenzene, 2-difluoromethyl-4-nitrochlorobenzene, and 2-trifluoromethyl-4-nitrochlorobenzene in a residual pot residue obtained from the rectification each had a content of 29.8 wt %, 59 wt %, and 9.6 wt %. The pot residue was returned to the fluorination for reuse, and a product obtained from a pot residue after reusing had an average molar yield of 94.5%.

Comparative Example 1

275 g of 2-trichloromethyl-4-nitrochlorobenzene (MW=274.9, 1.0 mol) and 136 g of triethylamine hydrofluoride (MW=121.2, 1.1 mol) were successively added into a three-necked flask, stirred, and heated to a temperature of 100° C. to 110° C., and then reacted at the temperature for 15 h. A resulting reaction product was then cooled, and filtered to obtain a triethylamine hydrochloride wet product and a filtrate. The triethylamine hydrochloride wet product was vacuum dried at 50° C. for 14 h under a vacuum degree of −0.08 MPa to obtain 196 g of a by-product triethylamine hydrochloride (the drying temperature was low and the residual 2-trifluoromethyl-4-nitrochlorobenzene was too much to be dried), while an evaporated gas during the drying was condensed to obtain recycled 2-trifluoromethyl-4-nitrochlorobenzene. The filtrate and the recycled 2-trifluoromethyl-4-nitrochlorobenzene were combined, and rectified by a rectification column, controlling a pressure within 200 Pa and a top temperature of 65° C. to 75° C. A positive boiling product was collected to obtain 186 g of 2-trifluoromethyl-4-nitrochlorobenzene with a purity of 99.6%. 2-monofluoromethyl-4-nitrochlorobenzene, 2-difluoromethyl-4-nitrochlorobenzene, and 2-trifluoromethyl-4-nitrochlorobenzene in a residual pot residue obtained from the rectification each had a content of 30 wt %, 58 wt %, and 9.0 wt %. The pot residue was returned to the fluorination for reuse, and a product obtained from a pot residue after reusing had an average molar yield of 78% (a slightly low yield).

The above descriptions are merely preferred embodiments of the present disclosure. It should be noted that a person of ordinary skill in the art may further make several improvements and modifications without departing from the principle of the present disclosure, but such improvements and modifications should be deemed as falling within the scope of the present disclosure.

What is claimed is:

1. A method for preparing a trifluoromethyl aromatic compound, comprising:
   mixing a trichloromethyl aromatic compound with an organic alkali hydrofluoride to obtain a mixture, and subjecting the mixture to fluorination to obtain a reaction solution, wherein a molar ratio of the trichloromethyl aromatic compound to the organic alkali hydrofluoride is in a range of 1: (1-3);
   subjecting the reaction solution to solid-liquid separation to obtain an organic alkali hydrochloride wet product and a filtrate, drying the organic alkali hydrochloride wet product, and condensing and recycling a gas generated during the drying to obtain a condensed product; and
   purifying the filtrate and the condensed product by rectification to obtain the trifluoromethyl aromatic compound;
   wherein the trichloromethyl aromatic compound comprises one selected from the group consisting of a trichloromethyl benzene compound and a trichloromethyl pyridine compound: the trichloromethyl benzene compound has a structure as shown in Formula I; and the trichloromethyl pyridine compound has a structure as shown in Formula II;

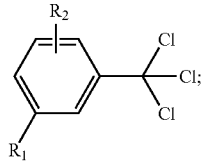

Formula I

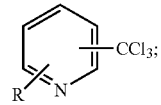

Formula II wherein
in Formula I: $R_1$ is halogen and $R_2$ is —$NO_2$; and in Formula II: R is halogen; and
under the condition that a pot residue obtained from the rectification comprises one or more selected from the group consisting of the trichloromethyl aromatic compound, a monofluoro substitute and a difluoro substitute thereof, the method further comprising: returning the pot residue obtained from the rectification to the fluorination for reuse.

2. The method of claim 1, wherein the organic alkali hydrofluoride comprises an organic amine hydrofluoride.

3. The method of claim 2, wherein the organic amine hydrofluoride comprises one or more selected from the group consisting of a pyridine hydrofluoride, a triethylamine hydrofluoride, a diethylamine hydrofluoride, a trimethylamine hydrofluoride, a dimethylamine hydrofluoride, and a monomethylamine hydrofluoride.

4. The method of claim 1, wherein the fluorination is conducted at a temperature of 80° C. to 140° C. for 5 h to 20 h.

5. The method of claim 1, wherein the drying is conducted by vacuum drying, and the drying is conducted at a temperature of 70° C. to 80° C. under a vacuum degree of −0.09 MPa to −0.095 MPa for 10 h to 16 h.

6. The method of claim 1, wherein an organic alkali hydrochloride is obtained by drying; and the organic alkali hydrochloride is neutralized with a liquid alkali to obtain a neutralized product, and the neutralized product is subjected to distillation and dehydration to obtain a free organic alkali.

7. The method of claim 1, wherein purifying the filtrate and the condensed product by rectification is conducted at a vacuum degree of 100 Pa to 200 Pa, and a top temperature of the rectification is at a temperature of 80° C. to 100° C. below the boiling point of the trifluoromethyl aromatic compound.

* * * * *